US010850094B2

(12) United States Patent
Molsberger

(10) Patent No.: US 10,850,094 B2
(45) Date of Patent: Dec. 1, 2020

(54) DC OUTPUT APPARATUS WHICH CAN BE USED FOR THERAPEUTIC PURPOSES

(71) Applicant: Albrecht Molsberger, Duesseldorf (DE)

(72) Inventor: Albrecht Molsberger, Duesseldorf (DE)

(*) Notice: Subject to any disclaimer, the term of this patent is extended or adjusted under 35 U.S.C. 154(b) by 0 days.

(21) Appl. No.: 14/359,579

(22) PCT Filed: May 27, 2013

(86) PCT No.: PCT/EP2013/060893
§ 371 (c)(1),
(2) Date: May 21, 2014

(87) PCT Pub. No.: WO2013/175021
PCT Pub. Date: Nov. 28, 2013

(65) Prior Publication Data
US 2015/0073406 A1 Mar. 12, 2015

(30) Foreign Application Priority Data
May 25, 2012 (DE) .......................... 10 2012 010 262

(51) Int. Cl.
*A61N 1/20* (2006.01)
*A61B 18/12* (2006.01)
*A61B 18/14* (2006.01)
*A61N 1/05* (2006.01)

(52) U.S. Cl.
CPC ............ *A61N 1/20* (2013.01); *A61B 18/1206* (2013.01); *A61B 18/1477* (2013.01); *A61N 1/0502* (2013.01); *A61N 1/205* (2013.01); *A61B 2018/1266* (2013.01); *A61B 2018/1425* (2013.01); *Y10T 29/49117* (2015.01)

(58) Field of Classification Search
CPC .............. A61N 1/0551; A61N 1/36007; A61N 1/36017
See application file for complete search history.

(56) References Cited

U.S. PATENT DOCUMENTS

| | | | |
|---|---|---|---|
| 3,842,841 A | 10/1974 | Brighton et al. | |
| 4,837,049 A * | 6/1989 | Byers | A61B 5/0422 216/11 |
| 4,913,148 A | 4/1990 | Diethelm | |
| 5,425,752 A | 6/1995 | Vu'Nguyen | |
| 5,439,440 A | 8/1995 | Hofmann | |
| 6,277,116 B1 | 8/2001 | Utely et al. | |
| 2001/0046653 A1 | 11/2001 | Legarde | |
| 2004/0010290 A1 | 1/2004 | Schroeppel et al. | |
| 2004/0097918 A1 | 5/2004 | Schonfeld | |
| 2004/0111128 A1 | 6/2004 | Wang | |
| 2004/0167458 A1 | 8/2004 | Draghia-Akli et al. | |
| 2004/0249373 A1 | 12/2004 | Gronemeyer et al. | |
| 2005/0182457 A1 | 8/2005 | Thrope et al. | |
| 2005/0209565 A1 | 9/2005 | Yuzhakov et al. | |
| 2006/0111705 A1 | 5/2006 | Janzen et al. | |
| 2007/0060989 A1 * | 3/2007 | Deem | A61B 18/1477 607/99 |
| 2007/0213771 A1 * | 9/2007 | Spinner | A61M 19/00 607/2 |
| 2007/0242743 A1 | 10/2007 | Scherman | |
| 2008/0312647 A1 * | 12/2008 | Knopp | A61B 18/1477 606/41 |
| 2010/0049192 A1 * | 2/2010 | Holtz | A61B 18/1492 606/41 |
| 2012/0289856 A1 * | 11/2012 | Motogi | A61B 5/0492 600/554 |

FOREIGN PATENT DOCUMENTS

| | | |
|---|---|---|
| DE | 37 19 353 A1 | 12/1988 |
| DE | 201 09 099 U1 | 8/2001 |
| DE | 101 29 912 A1 | 1/2003 |
| DE | 10 2004 055 866 A1 | 6/2006 |
| JP | 63-131605 A | 6/1988 |
| JP | H02-51564 U | 4/1990 |
| JP | 2003-501162 A | 1/2003 |
| JP | 2003-93521 A | 4/2003 |
| JP | 2007-268293 A | 10/2007 |
| JP | 2009-525057 A | 7/2009 |

OTHER PUBLICATIONS

G. Stux et al.: "Akupunktur—Lehrbuch und Atlas", Springer Verlag, vol. 3, p. 3 (1989).
G. Stux et al.: „Akupunktur—Lehrbuch und Atlas, Springer Verlag, vol. 6, p. 273 (2003).
J.-S. Han: "What is the Best Parameters of Electroacupuncture (EA) Stimulation for the Treatment of Pain and Drug Addiction", International Council on Medical Acupuncture and Related Techniques, http://www.icmart.org/index.php?id=198,0,0,1,0,0, pp. 1.

* cited by examiner

*Primary Examiner* — Michael J D Abreu
(74) *Attorney, Agent, or Firm* — Sughrue Mion, PLLC

(57) ABSTRACT

A direct current application device includes a direct current source or an appliance configured to be linked to a direct current source. A first electrode is configured to be connected to the direct current source. The first electrode comprises a plurality of needles comprising 3-12 needles which are configured to comprise an electrically conductive connection with each other. A second electrode is configured to be connected to the direct current source. The second electrode comprises a flat electrode, a needle, or a plurality of needles which are configured to comprise an electrically conductive connection with each other. A current device is configured to maintain a current at a constant level during an application of the direct current, or a battery as the direct current source.

14 Claims, No Drawings

DC OUTPUT APPARATUS WHICH CAN BE USED FOR THERAPEUTIC PURPOSES

CROSS REFERENCE TO PRIOR APPLICATIONS

This application is a U.S. National Phase application under 35 U.S.C. § 371 of International Application No. PCT/EP2013/060893, filed on May 27, 2013 and which claims benefit to German Patent Application No. 10 2012 010 262.3, filed on May 25, 2012. The International Application was published in German on Nov. 28, 2013 as WO 2013/175021 A1 under PCT Article 21(2).

FIELD

The present invention relates to a device for applying a direct current. The direct current application device according to the present invention can be used for the treatment of the human or animal body by therapy or for the cosmetic treatment thereof. The present invention is moreover directed to the direct current application device for specific application in certain methods for treatment of the human or animal body by therapy. The direct current application device according to the present invention is particularly suitable for treatment of inflammations and/or pain. The present invention also relates to a kit and a method for producing the direct current application device.

BACKGROUND

Many medically or cosmetically relevant impairments of the human or animal body are local. There is a medically relevant impairment in the case of diseases or disorders of the function of the body. A treatment by therapy is, in principle, indicated in these cases. In the case of irritations, which, within the scope of the present invention, is understood to mean relatively minor impairments or complaints of the human or animal body which do not constitute a disease or functional disorder and which are not worthy of therapy, at least a cosmetic, non-therapeutic treatment is often expedient.

The present invention relates to both the non-therapeutic, cosmetic treatment of cosmetic impairments caused by (predominantly local) irritations and the development of novel therapy options for (predominantly local) medically relevant impairments of the human or animal body.

The term therapy here also includes prophylaxis. "Local" means that a certain area of the irritation or the medically relevant impairment can be determined on or in the body. This area is, for example, locally circumscribed and, for example, exactly identifiable. The area (for example, area of irritation, area of inflammation, area of pain) is accompanied by specific symptoms and triggers the impairment or the complaints, or is associated therewith.

Impairments of the human or animal body, which are caused by local inflammation or pain states, are, for example, aseptic inflammations, often caused by local overloads (distortions, tendinitis), or else neuropathic pain. In the orthopedic sector, local inflammation and pain states occur, for example, in conjunction with tissue injuries, for example, of muscles (for example, muscle traumas), nerves, skin or holding apparatus, vessel injuries or else in conjunction with nerve inflammations, inflammations of the tendons or bones or scar formation. There often exists a locally circumscribed area in which the complaints can be determined.

If an impairment satisfies the criterion of a disease or disorder of the function of the body, it is generally indicated to be treated by therapy. By contrast, examples of a merely cosmetically relevant impairment include formation of wrinkles, for example, caused by increased muscular tension, poor and alleviating postures, or merely cosmetically impairing skin changes such as, for example, reddening.

Methods and means for treatment of medically or cosmetically relevant impairments and complaints by therapy or cosmetics are known per se. Even if, for example, physiotherapy can provide relief in some cases, specific pharmaceutical active ingredients are generally, however, used therefor, primarily cortisone, non-steroidal anti-inflammatory drugs, analgesics and related substances. In addition to the desired (local) effect, these usually also have undesirable local side effects (such as aseptic inflammations in the case of local application of cortisone) and/or systemic side effects, and can have an adverse influence on the metabolism and hormone balance. In many cases, the conventional methods for therapy cannot prevent a chronic course of disease. It is therefore expedient to consider alternatives to the use of (exogenous) active ingredients.

Therapy options which make increased use of the intrinsic healing capacities of the human or animal body are also known. A widespread technique is acupuncture, which is traced back to traditional Chinese medicine (TCM), and developments thereof.

Acupuncture has been generally acknowledged as effective and low risk for the treatment of specific complaints, such as chronic pain (for example, headache, migraine). Thus, for example, all German statutory health insurers have been paying for acupuncture treatment in the case of chronic lower back pain and chronic knee pain in the case of gonarthrosis since Jan. 1, 2007, in particular due to the results of large prospective and randomized trials (GERAC, German Acupuncture Trials). Private health insurers pay for acupuncture services for pain treatment and, after a review on a case-by-case basis, usually also for further indications. The "Cochrane Reviews" from 2009 describe acupuncture as "a valuable non-pharmacological therapy option in the case of patients with frequent, episodic tension headache" and note that "acupuncture is at least as effective, possibly even more effective, than a medicament-based prophylactic therapy in the case of migraine, while having fewer undesired effects".

The GERAC studies showed that there was no significant difference between acupuncture at points following the prescriptions from TCM and acupuncture at other points (so-called "pseudo-acupuncture"). Positive therapeutic or cosmetic effects have been shown for both forms of acupuncture when applied to local inflammation and pain states. These days, forms of acupuncture are also common, which do not orient themselves on the traditional theoretical background of TCM.

Endogenous physiological electric fields are known from biology. Such fields lie in the region of 70 mV/mm (nerve growth in chickens), 140 mV/mm (wound healing in rats), 600 mV/mm (eye lens of vertebrates) to 1500 mV/mm (development of the neural tube in the Axolotl amphibian). Depending on the internal resistance of the relevant biological tissue, this results in currents of 10-200 μA. Endogenous electric fields are built-up for a period of time of hours to weeks, for example, in the region of the wound, in the region of the active cell growth, and in the case of cell migration, and appear to be essential for regulating cell behavior.

The use of exogenous electric fields in medicine and cosmetics is generally known. Use is here made of regular strong and/or time-varying fields, wherein the temporal variation is brought about by, for example, an AC voltage or short DC voltage pulses. These strong electric fields previously used in therapy are produced by, for example, high voltages and, regularly, by strong currents. In this context, use is made of alternating current and pulse current instruments in order to counteract electrolytic effects on the employed electrodes and, for example, on the body tissue.

By way of example, the transcutaneous electrical nerve stimulation (TENS) is known. Low-frequency (1-100 Hz) two-phase alternating current pulses are here used for alleviating pain, primarily for short-term "electric analgesis". The voltage is up to 70 V with a pulse duration of approximately 250 µs, with the current being up to approximately 90 mA. The effect is based primarily on an increase in the central release of endorphins. It is unclear whether local and longer-term effects are obtained in the affected tissue.

Electroacupuncture is also known. The mode of action thereof is directed to releasing central pain-alleviating substances, for example, enkephalins, endorphins and dynorphins.

US 2004/0111128 A1 describes electroacupuncture using alternating currents. In electroacupuncture, use is made of a low-frequency stimulating current (Springer Lexikon der Medizin [Encyclopedic dictionary of medicine]); the frequency of the electric signal is here fixed or variable (2-10 000 Hz) Like in TENS, use is here made of relatively strong currents which lie between 2 and 15 mA. At this intensity, these can only be applied in pulsed form, with a pulse duration of approximately 0.3-0.6 ms. In order to avoid electrolytic effects at the transition between electrode and biological tissue at these high currents, the polarity is changed (alternating current). The electric parameters in electroacupuncture in any case accordingly comprise frequency and intensity.

In conclusion, the known instruments for TENS or electroacupuncture have complicated circuitry and operate at high currents, short pulses, and alternating current at specific frequencies. Irrespective thereof, the stimulation dose is often uncontrollable. These means and methods in the prior art are directed to alleviating pain, which is based upon a central analgesic effect. These are not directed to a local effect (such as an inflammation-inhibiting or regeneration-promoting effect).

Direct current galvanotherapy with high currents of 60-80 mA at a voltage of 6-35 V is known in tumor therapy. The aim of this therapy is a destruction of the tumor tissue, for example, by necrosis. A destruction of tissue is not therefore an undesired effect to be avoided, but, by contrast, expressly desired. The method makes use of the increased conductivity of tumor tissue compared to healthy tissue, and so the current flow is intended to concentrate selectively in the tumor tissue and cause the disintegration of the tumor there by electrolytic and necrotic effects.

Direct current is also used for transcutaneous transport of ionizable medicaments (iontophoresis). Use is made of voltages of approximately 36-60 V and currents of approximately 10-30 mA. In order to avoid local tissue damage in this case and in order to be able to transport a high dose of active ingredients by electrophoretic means, large-area skin electrodes are placed onto the skin.

An application of wide-area, damp cellulose electrodes on the scalp for stimulating the central nervous system is furthermore known, for example, in the case of tinnitus (transcranial direct current stimulation, tDCS). Use is here made of a current of up to 1 mA and a voltage of 8-25 V, in the case of constant and pulsing current.

It is known that the corresponding electric fields produced by weak direct current promote the vessel growth, inter alia by releasing VEGF and the effect thereof on endothelial cells. They lead to the movement and rearrangement of cell membrane receptors, increase the division rate of specific cells and accelerate the cell migration of epithelial cells. This cell migration is away from the anode (from the positive pole) and to the cathode (to the negative pole). Animal experiments have provided indications that the peripheral nerve regeneration after spinal injury can be accelerated, wherein the axons of the nerve cells grow towards the cathode, which has to lie toward the head over a period of approximately three weeks. Clinical studies on humans indicate an acceleration of wound healing by electric fields.

SUMMARY

An aspect of the present invention is to provide means and methods, by means of which local impairments of the human or animal body, for example, those caused by inflammations and/or pain, can be alleviated or removed.

An additional aspect of the present invention is for the means and methods to provide a more effective, safer, more reproducible and/or fewer side effects causing application, and/or have a longer-term effect than the means and methods of the prior art.

An aspect of the present invention is to provide a direct current application device which includes a direct current source or an appliance configured to be linked to a direct current source. A first electrode is configured to be connected to the direct current source. The first electrode comprises a plurality of needles comprising 3-12 needles which are configured to comprise an electrically conductive connection with each other. A second electrode is configured to be connected to the direct current source. The second electrode comprises a flat electrode, a needle, or a plurality of needles which are configured to comprise an electrically conductive connection with each other. A current device is configured to maintain a current at a constant level during an application of the direct current, or a battery as the direct current source.

DETAILED DESCRIPTION

In an embodiment, the present invention provides a direct current application device comprising a direct current source or an appliance to be linked to a direct current source, and a first electrode and a second electrode to be connected to the direct current source, characterized in that the direct current application device either comprises a means for keeping the current at a constant level during the application of the direct current (for example, in the case where there is a change of a resistance applied between the electrodes), or the direct current source is a battery, and in that the first electrode and the second electrode are, independently of one another, embodied either (i) as a flat electrode (for example, an adhesive electrode) or (ii) as a needle or a plurality of needles electrically conductively connected to one another. An example of a direct current application device according to the present invention is where the first electrode is embodied as a flat electrode (for example, an adhesive electrode) or as a needle or a plurality of needles electrically conductively connected to one another and the second electrode is embodied as a flat electrode (adhesive electrode).

Within the scope of the present invention, the term "battery" also comprises rechargeable batteries and galvanic cells, either on their own or, for example, in a two-fold, three-fold or four-fold embodiment connected in series, in addition to batteries with a voltage of, for example, 1.2 V (for example, nickel-metal hydride batteries) to 1.5 V (for example, alkali-manganese or zinc-carbon batteries).

In the present case, an "adhesive electrode" is understood to mean a flat electrode which can be applied to the (possibly depilated) skin surface and can be fastened there (possibly using an additional material such as electrode gel or an electrode paste which imparts or improves the conductivity), for example, by adhesive bonding.

For the purposes of the present application, a flat electrode is also occasionally referred to as a "pad".

In an embodiment, the present invention provides the direct current application device according to the present invention for use in the treatment of inflammations and/or pain, for example, of the muscles, nerves, tendons or bones.

Expressed differently, the subject matter of this embodiment of the present invention is also the use of the direct current application device according to the present invention for the treatment of inflammations and/or pain, for example, of muscles, nerves, tendons or bones, or the use of the direct current application device according to the present invention for the production of a therapeutic device for the treatment of inflammations and/or pain, for example, of muscles, nerves, tendons or bones. This aspect of the present invention also relates to a method for the treatment of inflammations and/or pain, for example, of muscles, nerves, tendons or bones of a patient, which comprises allowing the direct current application device according to the present invention to act on the body of the patient.

In an embodiment, the present invention provides a kit for producing a direct current application device according to the present invention (for example, as described above), comprising: a flat electrode (for example, adhesive electrode), a needle or a plurality of needles for use as a first electrode, a flat electrode (for example, adhesive electrode), a needle or a plurality of needles for use as a second electrode, either a means for keeping the current at a constant level during the application of direct current by a direct current source (for example, in the case where there is a change of a resistance applied between the electrodes) or a direct current source which is a battery, and optionally means for an electrically conductive connection for a plurality of needles.

The term "comprising" also includes the meaning "consisting of" except if something else necessarily emerges from the context of the present invention. A corresponding statement applies to term variants such as, for example, "comprise" and "consist of".

In the present case, direct current is understood to mean electric current, the direction of which does not change and the time-averaged current of which substantially has no change under unchanging conditions. The direct current can, for example, be a "pure" direct current, the current of which does not change substantially or at all under unchanging conditions. Certain time variations are also, however, possible, for example, a "pulsating" direct current, in which the current periodically oscillates around a certain average value, without, however, the current direction changing in the process. The direct current can therefore, for example, be a direct current undulating around a previously set (for example, constant) value. The undulation can, for example, occur with a frequency of between 0.001 and 10 Hz, for example, between 0.01 and 1 Hz, for example, 0.1 Hz. It can, for example, be rectangular, sawtooth-shaped and sinusoidal. The deflection of the direct current here can, for example, be 50% of the previously set value (i.e., the values change between 150% and 50% of the previously set value), for example, 40%, 30%, 20%, 15%, 10%, 7.5%, 5%, 2.5% or 1%.

The present invention is based on the discovery that a weak direct current can improve the aforementioned medically or cosmetically relevant impairments and complaints if it acts via an electrode in a local electric DC voltage field on the body. The effects already occur if the direct current is very weak. A particularly well reproducible effect can be obtained if the direct current is constant. Depending on the application, needle-shaped or else flat electrodes obtain particularly good effects (for example, two needle-shaped electrodes, two flat electrodes or else a needle-shaped electrode in combination with a flat electrode, wherein a needle-shaped electrode optionally comprises a plurality of needles and/or a flat electrode optionally comprises a plurality of flat structures). The applied electric field according to the present invention is of the order of endogenous and physiological electric fields.

The use of one or more needles as an electrode can be advantageous. Keeping the current at a constant level can also be advantageous. The current determines the strength of the electric field in the tissue. In the case of a constant current (in contrast to, for example, setting a constant voltage), possible variations of the resistance cannot cause variations in the current and, in particular, cannot cause current peaks. Even interindividual differences in resistance cannot (in contrast to setting a constant voltage) lead to different currents. It was found that the treatment results obtained vary to a certain extent from case to case in the case of a non-constant current, without, however, calling the basic treatment success into question.

The direct current application device (as described above) according to the present invention can, for example, comprise a means for keeping the current at a constant level during the application of the direct current (for example, in the case where there is a change of a resistance applied between the electrodes). This means is embodied to keep the current constant when applying the direct current, in particular when the resistance applied between the electrodes changes. Without such a means, there often is a situation where the electric resistance of the body tissue (for example, of the skin) changes during the treatment and then there is variation in the current. It is a discovery of the present invention that the result is particularly well reproducible when a means for keeping the current at a constant level is used. Such a means provides a constant current flow, even in the case of a changing resistance, and an unchanging treatment success is achieved thereby. It was moreover found that, without a means for keeping the current at a constant level, different currents can be observed in different individuals due to an individually different resistance between skin and tissue, which usually lies in the range of 3-40 kΩ, and, as a result thereof, the treatment successes vary to a certain extent. When using the means for keeping the current at a constant level, the unchanging treatment success is obtained independently of the individually different resistance between skin and tissue.

The direct current application device according to the present invention renders it possible to improve or remove cosmetically or medically relevant impairments and complaints of the body. These can, for example, be inflammations and/or pain and can, for example be local. According to the present invention, the use of exogenous pharmaceutical active ingredients and medicaments can be reduced or completely avoided. As a result, the undesired side effects of such substances occur to a reduced extent or do not occur at all. The impairments and complaints are alleviated or removed permanently or at least long-term when using the direct current application device according to the present invention, or these are prevented. If the application is repeated, the effect can often be increased to permanent freedom from the impairments.

The use of the direct current application device according to the present invention is low risk, effective and has few or no side effects. The effect occurs in a fast and predictable manner. The applied current dose is exactly controllable. It is moreover advantageous that, according to the present invention, a regeneration of tissue damaged by chronic inflammations or degenerative processes is also allowed. According to the present invention, the effectiveness against inflammations and pain is improved significantly compared to electroacupuncture according to the prior art.

The direct current application device according to the present invention has, in particular, an antiphlogistic and analgesic effect when applied to the human or animal body, which effect can be advantageous, for example, in the case of treatment of (in particular local) inflammations and pain, particularly of the muscles, nerves, tendons or bones. It is possible to treat, for example, aseptic inflammations, nerve pain (for example, neuropathic pain), headache and orthopedic indications, such as pain in the thoracic spine or shoulder, back pain or tendon pain (such as tennis elbow). The inflammations/pain can, for example, be in conjunction with tissue injury (for example, muscles, nerves, skin or holding apparatus, vessels), nerve inflammations, inflammations of the tendons or bones and scar formation.

The direct current application device according to the present invention enables a treatment concept which builds from acupuncture. It can be applied separately or included within the usual context of an acupuncture treatment. Such a concept can develop acupuncture and thus improve the appropriate treatment by therapy, or cosmetic treatment, of complaints or impairments.

According to the present invention, the direct current application device according to the present invention can be used for human or animal bodies of patients. The term "patient" should not be understood as restrictive to a treatment by therapy, but to also cover a cosmetic treatment. Patients can, for example, be mammals such as horses, dogs, cats, camels and humans.

During a typical course of treatment, the painful/inflamed region is initially localized. By way of example, the region is pierced by one or more (metal) needles, which are optionally electrically connected to one another. The tip(s) of the needle(s) can lie on, or outside of, acupuncture points. The needle(s) is/are connected to a terminal as a first electrode, for example, to the negative terminal of the direct current source. The other terminal is connected to the second electrode, which can, for example, be a surface-adhering electrode on a different region of the body. Such a surface electrode ("pad") can, for example, be placed over large groups of muscles or layers of fat so that it is not the case that individual nerves are stimulated by the surface electrode. A constant current can, for example, be applied for the treatment. The pain or the inflammation typically abates approximately 2 hours after the treatment.

The keeping of the current at a constant level can, for example, be performed via an automated keeping at a constant level. The direct current application device according to the present invention can, for example, accordingly contain an automated means for keeping the current at a constant level when applying the direct current (for example, in the case where there is a change of a resistance applied between the electrodes).

The electric resistance R during the treatment is primarily determined by the contact of the electrodes with the skin and, possibly, by the direct vicinity of the needle(s). The resistance often changes during the course of the treatment. In order nevertheless to provide an unchanging current I, there is, inter alia, the option of changing the contact area between electrodes and body tissue, for example, by changing the contact pressure of the second electrode, or of changing an internal resistance of the direct current application device according to the present invention.

The constancy of the current I can, for example, be provided by an appropriate change in the voltage U.

A means for keeping the current at a constant level in the direct current application device according to the present invention can, for example, be automated and configured as a controller which can be set up, for example, from analog components or as an integrated circuit. Such a controller can, for example, comprise a means for measuring the actual current (for example, in the feed line to the first electrode), a means for determining a deviation from a predetermined intended current, and a means for setting a correction of the voltage U corresponding to the deviation, for example, proportional to the deviation (proportional controller).

Direct current sources according to the present invention can, for example, be batteries (as defined above). A battery can, for example, have a voltage of between 1.2 and 1.5 V and be present on its own or, for example, in a two-fold, three-fold or four-fold embodiment connected in series. Batteries can, for example, be used when there is no means for keeping the current at a constant level when applying the direct current in order to produce a particularly simple but nevertheless already effective direct current application device. Batteries can, however, alternatively also be used in conjunction with a means for keeping the current at a constant level when applying the direct current. Further direct current sources include power supply units or constant current sources. A direct current source can, for example, be contained in, for example, the appliance sold under the name "DC-Stimulator" by neuroConn GmbH (Ilmenau, Germany). In the prior art, this appliance is used for transcranial direct current stimulation (tDCS) of the brain. It comprises an automated means for keeping the current at a constant level and is offered in a kit together with two sponge electrodes for application on the head for transcranial direct current stimulation, but not for electroacupuncture. The contained current source differs to the current sources used for electroacupuncture in the prior art since it supplies direct current instead of alternating current, and the applied current is moreover substantially lower.

The direct current application device according to the present invention can, for example, comprise a modifiable internal resistance for setting the applied current.

According to the present invention, a needle is understood to mean an elongate (for example, cylindrical) body, the length of which is large compared to the diameter. A needle can, for example, have a tapered end, for example, a conically tapered one. The needle or needles for use as first electrode can, for example, be provided so that the human or animal body is not injured by the application thereof. The diameter of a region for penetration (without considering a tapered end) lies, for example, between 0.1 and 0.8 mm, for example, between 0.2 and 0.4 mm and, for example, is approximately 0.3 mm, wherein a the region for penetration can, for example, moreover have a tapered end; the length of a region for penetration can, for example, lie between 10 and 100 mm, for example, between 20 and 50 mm and, for example, is approximately 30 mm. The diameter in a holding region can, for example, be approximately 1-3 mm in order to provide a simple connection of a plurality of needles. Needles can, for example, have the shape of known acupuncture needles and have the following dimensions: 0.2×15 mm, 0.25×40 mm, 0.3×30 mm, 0.3×100 mm, 0.35×50 mm.

The material of needle(s) for use as first electrode can, for example, be metal. Metals can, for example, be stainless steels, i.e., unalloyed or alloyed steels with low sulfur and phosphorus content. Further alloy components can, for example, be chromium (for example, with a proportion of 10.5-13% by weight or higher), nickel (for example, with a low proportion, for example, at most 10% by weight), molybdenum, titanium and/or niobium. An 18/10 chromium-nickel steel or medical stainless steel can, for example, be used. Steels can, for example, be those which are resistant to water and weak organic and inorganic acids. Corrosion-resistant steels can, for example, be used. Further metals are, for example, silver, gold and platinum. The needles are optionally merely silver-plated, gold-plated or platinum-plated. Sintering materials, for example, of silver/silver chloride, can also be used.

The first electrode can, for example, comprise a plurality of needles, for example, 3-12, for example, 4-10, 6-10, 6-8 and, for example, 8. This allows for a particularly good encircling of a region to be treated. In special embodiments, the first electrode can also comprise a larger number of needles, which can be advantageous if more than one region to be treated is present.

In the case of using a plurality of needles as a first electrode, the tips of the needles can, for example, be arranged along a substantially circular or elliptical circumference in the direct current application device. The second electrode can, for example, lie outside of the region circumscribed by the needles. The electrically conductive connection of the needles along the (circular or elliptical) circumference can, for example, be embodied in such a way that the circuit of the needles of the first electrode is an ordered series circuit and not a zigzag circuit. These embodiments provide for advantageous treatments.

As an alternative thereto, the needles can also be arranged along a substantially straight line.

In an embodiment of the present invention, provision can also be made for a first group of needles and for one or more further group(s) of needles (for example, two, three, four or five groups of needles as first electrode), which allows the treatment of more than one region to be treated. In these embodiments, the tips of the needles of the first group can, for example, be arranged along a substantially circular or elliptical circumference, and the tips of the needles of the further group(s) to (in each case) likewise be arranged along a substantially circular or elliptical circumference. The second electrode can here, for example, lie outside of the regions circumscribed by the needles. The electrically conductive connection of the needles can, for example, be embodied along the respective (circular or elliptical) circumference of the individual groups of needles (series connection of the needles of the respective group) and/or for the groups to be connected in series by in each case a single electrically conductive connection.

As an alternative thereto, the tips of the needles in the first group can be arranged along a substantially straight line and the tips of the needles in the further group(s) can (in each case) likewise be along a substantially straight line, wherein, the needles in the individual groups can, for example, respectively be connected in series and/or the groups are connected in series by in each case a single electrically conductive connection.

The first electrode (electrode for use in the region to be treated, for example, needle electrode) can, for example, be embodied as a cathode (negative pole) and the second electrode can, for example, be embodied as an anode (positive pole). This optimizes the treatment possibilities when using the direct current application device according to the present invention.

In an embodiment of the present invention, the first electrode can also be embodied as flat electrode (for example, as an adhesive electrode) (optionally as a plurality of flat structures, for example, two, three, four or five). The statements made in the following for a flat second electrode (variant A) apply to embodiments of a flat first electrode. To the extent that the second electrode is likewise embodied as a flat electrode, the (overall) area of the second electrode can, for example, be greater than the (overall) area of the first electrode, for example, greater by at least 50%, 100%, 200%, 400%, 1000% or 5000%. Sizes of a flat first electrode can, for example, be 0.5 to 5 cm$^2$, for example, 1 cm$^2$ to 2 cm$^2$.

The second electrode can, for example, be embodied as a flat electrode (variant A). Such an electrode can be used as a surface electrode and can, for example, be adapted to being applied to the body surface, for example, by an embodiment as an adhesive electrode (as defined above). An electrode which is worked into an adhesive strip, or connected differently by means of an adhesive strip, can, for example, be provided. An adhesive effect can also be imparted by electrode gel or electrode paste. The material for the second electrode can, for example, be selected from the group consisting of conductive rubber, conductive textile, conductive plastic, a sponge (to be soaked with, for example, water or saline solution), a sintering material (such as silver/silver chloride) and metal (for example, stainless steel, silver, gold and/or platinum).

The sizes of a flat second electrode can, for example, be 25 cm$^2$ to 200 cm$^2$, for example, 50 cm$^2$ to 100 cm$^2$.

Without being bound to a specific theory, the assumption is made that the use of silver/silver chloride electrodes stabilizes the junction potential at the metal/electrolyte transition, particularly in a chloride-containing medium such as the body surroundings, so that the current application becomes even more controllable.

The second electrode optionally comprises a plurality of flat structures as described above, for example, two, three, four or five.

It is additionally also possible to embody the second electrode as a needle (variant B), wherein the statements made about the needles of the first electrode also apply to embodiments of this needle.

Combinations of the first and second electrode are as follows: needle-shaped first electrode in combination with needle-shaped second electrode, needle-shaped first electrode in combination with flat second electrode, flat first electrode in combination with needle-shaped second electrode and flat first electrode in combination with flat second electrode. The statements made above in respect of needle-shaped electrodes and flat electrodes apply. A needle-shaped electrode optionally comprises, for example, a plurality of needles (for example, two, three, four or five) and/or a flat electrode optionally comprises a plurality of flat structures (for example, two, three, four or five).

In an embodiment of the present invention, both electrodes can, for example, be unified in a single structure (multi-pole needle or multi-pole flat structure). By way of example, this can be advantageous when treating a spatially tightly circumscribed region or in the case of patients who, in general, tolerate the application of electrodes badly. According to the present invention, a needle can thus have the first electrode and the second electrode in series along the longitudinal extent thereof, for example, the cathode closer at the end for penetration than the anode, or else the anode closer at the end for penetration than the cathode. The cathode and/or the anode are in this case furthermore either continuous or discontinuous. By way of example, the surface of the cathode and/or the anode can optionally be embodied as one or more cylinder jackets.

The electrodes, the means for connecting the electrodes to the direct current source and/or the terminals of the direct current source can, for example, be characterized in accordance with the polarity, for example, by color or shape, symbols such as + and −, numbers or letters.

A physiologically acceptable current or a current which does not damage the cells of the body tissue can, for example, be applied. In the variant A with a flat second electrode, the maximum current of the direct current can, for example, be 2000 µA, for example, 1000, 700, 500, 400, 300, 250, 200, 150 or 100 µA (in the case of a needle-shaped or flat first electrode). In variant B, with a needle as second electrode, the maximum current of the direct current can, for example, be 1000, 750, 500, 250, 200, 150, 100, 50, 25 or 5 µA (in the case of a needle-shaped or flat first electrode). It is applicable both in variant A and in variant B that the highest of the aforementioned currents can, for example, be selected in the case of the flat first electrode and the lower selection is made in the case of the needle-shaped first electrode. The minimum current of the direct current can, for example, be (in the case of a needle-shaped or flat first electrode) 10, 20, 30, 40 or 50 µA (variant A) or 1, 1.5, 2 or 2.5 µA (variant B). Regions for the current of 10-250 µA, 20-250 µA, 10-200 µA, 20-200 µA, 10-150 µA, 20-150 µA, 30-150 µA, 20-100 µA, 30-100 µA, 40-100 µA and 50-100 µA (variant A) or regions of 1-25 µA, 1.5-20 µA, 2-15 µA, 2-10 µA and 2.5-5 µA (variant B) can, for example, be applied (in the case of a needle-shaped or flat first electrode). The direct current application device according to the present invention can, for example, comprise a means for setting the current and, for example, a means for setting a minimum and/or maximum current, for example, remotely controllable in all cases.

The current density, defined as applied current in relation to the area contacted by a needle, can, for example, be at most 10 µA/mm$^2$, for example, at most 7 µA/mm$^2$, at most 5 µA/mm$^2$, at most 3 µA/mm$^2$, at most 2.5 µA/mm$^2$, at most 2 µA/mm$^2$, at most 1.5 µA/mm$^2$, at most 1 µA/mm$^2$ or at most 0.5 µA/mm$^2$. The electric voltage when using the direct current application device for treating the human or animal body can, for example, be at most 5 V, 4.8 V, 4.5 V, 4 V, 3.6 V, 3 V, 2.5 V, 2.4 V, 2 V, 1.5 V or 1.2 V. This provides that damaging effects on the body are avoided. The direct current application device according to the present invention can, for example, comprise an (for example, remotely controllable) means for setting a maximum voltage. It can furthermore, for example, comprise an (for example, remotely controllable) means for setting a maximum charge.

The strength of the electric field can, for example, be in the region of 10-2500 mV/mm, for example, of 200-1500 mV/mm. The field density can be even higher in the vicinity of needle-shaped electrodes; this being a treatment principle using, for example, the direct current application device according to the present invention. Strength and profile of the electric field in the surroundings of needle-shaped electrodes, when using the direct current application device according to the present invention, direct the effect primarily into the region in which the electrode is applied or in the direct vicinity thereof. The field strength reduces exponentially in an orthogonal direction in the direct vicinity of a needle-shaped electrode.

The direct current application device according to the present invention furthermore optionally comprises a means for temporal control, by means of which a plurality of periods of time for applying the direct current can be determined in advance. In the simplest case, this is an electronic switchable break in the electrically conductive connection between cathode, direct current source and anode. The means for temporal control can, for example, be linked to a means for setting a minimum period of time, wherein the latter can, for example, allow for the determining of a minimum period of time of 1 s, 10 s, 1 min, 2 min, 5 min, 10 min, 20 min or 30 min. The means for temporal control can, for example, be remotely controllable. In an embodiment of the present invention, the means for temporal control can, for example, furthermore be linked to a (for example, remotely controllable) means for determining a maximum period of time, wherein the latter can, for example, allow for the determining of a maximum period of time of 2 h, 1 h, 50 min, 40 min, 30 min, 20 min, 10 min, 5 min or 2 min.

The direct current application device according to the present invention can, for example, comprise an (for example, remotely controllable) means for ramping up and ramping down the current. At the beginning of the treatment, such a means allows an increase in the current from zero to the intended value within a predeterminable period of time (with a length of, for example, 1-60 seconds, for example, 5-45 seconds and, for example, 10-30 seconds) and, at the end of the treatment, it allows a drop from the intended value to zero within a predeterminable period of time (with a length of, for example, 1-60 seconds, for example, 5-45 seconds, for example, 10-30 seconds and, for example, 15 seconds). Slow ramping up and ramping down of the current can be advantageous because otherwise (in the case of a jump-like switching on or off of the current) the individual being treated feels an uncomfortable twitching or a feeling of an electric shock.

The direct current application device according to the present invention optionally comprises a (for example, remotely controllable) means for switching the polarity of the electrodes during a treatment. This can, for example, be linked to a means for temporal control so that it is possible, for example, to switch the polarity every second, every 10 s, every minute, every 2 min, every 5 min or every 10 min.

The direct current application device can optionally be set to a test mode in which a constant voltage of approximately 1-8 V, 2-6 V or 3-5 V is applied. This renders it possible to check whether or not the electrodes (for example, in particular, all needles) are correctly coupled electrically, or whether there is an occluded break in the cable in any one of the cables. The direct current application device can, for example, comprise a transducer (for example, a sound generator), which indicates whenever there is a correct current flow. From a lack of the signal, it is possible to deduce that the coupler chain is interrupted.

A transducer can, for example, be also be used to indicate the start and/or the end of the treatment. A transducer can furthermore be used, for example, to indicate whether the current flow is interrupted during a treatment or whether the impedance of the patient is too high, for example, in combination with a means for switching off.

With the aid of the test mode, it is also possible to stimulate the individual electrodes (for example, needles) directly and to deduce the correct positioning of the electrode (for example, needle) from the reaction of the patient (muscle twitching or pain in non-contractible tissue), as described in more detail below.

The kit according to the present invention for producing a direct current application device can, for example, additionally comprise instructions for the treatment of the human or animal body by therapy or for the cosmetic treatment thereof, wherein the treatment can, for example, correspond to the one explained in more detail below.

In an embodiment, the direct current application device according to the present invention comprises a direct current source, a first electrode and a second electrode to be connected to the direct current source, a means for keeping the current at a constant level when applying the direct current, a first electrode, which is embodied as a needle or a plurality of needles connected to one another in an electrically conductive manner, and a second electrode, which is embodied as flat electrode. A maximum DC current of 2000 µA, for example, 1000 µA, for example, 700 µA, and for example, 500 µA can, for example, be provided. The lower currents listed above can also be combined with this embodiment.

The direct current application device according to the present invention can, for example, be used in the treatment of inflammations and/or pain, for example, of the muscles, nerves, tendons or bones.

In the treatment, an application of a continuous current and an application of a pulsed current can, for example, be provided. An undulating current, as described above, or a non-periodically changing current (which substantially has the same value at all times) are alternatively possible. The current (or the value around which the current undulates) can, for example, be kept constant when applying the direct current, for example, also in the case where a resistance applied between the electrodes changes.

The duration of a treatment can, for example, lie between 1 min and 2 h, 5 min and 1 h, 10 min and 50 min, 20 min and 40 min, and, for example, be 30 min. The treatment can, for example, comprise an overall current application time of 60 min, 45 min, 30 min or 20 min. The current can, for example, be applied without interruption during the treatment. In an embodiment, the treatment can, however, for example, also comprise a plurality of predetermined periods of time (for example, 2, 3, 4, 5, 6 or more periods of time, for example, of equal length) during which the direct current is applied, wherein a pause of 1 s to 5 min, 10 s to 3 min or 30 s to 1 min can, for example, be provided between the periods of time. The direct current can alternatively be switched on and off with a frequency of 0.01-1 Hz, for example, 0.02 to 0.2 Hz and, for example, 0.05 to 0.1 Hz. These periods of time, or the switching on and off, are controlled by the optionally provided means for temporal control (see above). There can, for example, be a slow ramping up or ramping down of the current at the beginning and end of the treatment, for example, over a period of time of in each case 1-60 seconds, for example, 5-45 seconds, for example, 10-30 seconds, and, for example, 15 seconds.

The treatment can, for example, take place within one day, for example, within a period of time of 4, 3 or 2 hours. Depending on the treatment approach, the treatment can, for example, be carried out once or repeatedly (for example, one time, two times or three times per week, or daily).

In the run-up to the current application, the painful/inflamed region to be treated can, for example, be encircled and thus localized, for example, by deep feeling to the bone from all sides. Using the terminology of TCM, a corresponding point that hurts under pressure is referred to as "ah shi". The region to be treated is provided with an electrode after optional disinfection, for example, with one or more needles (for example, by penetration) and, for example, circumscribed by a plurality of needles (for example, in a circular or elliptical manner). Circumscribed here means, for example, that the needles are placed along the edge of this region. Further options consist of placing the needles a few millimeters outside of the edge, or else within the region. The aforementioned penetration by the needle(s) can, for example, be as deep as possible (for example, into the subcutaneous tissue, into muscle, into the ligaments or tendons, under the acromion, onto the facets of the spine or onto the bone skin), optionally after local anesthesia. As an alternative thereto, the region to be treated can also be provided with needles by arranging a plurality of needles along a substantially straight line, wherein this line intersects with, or touches, this region, or else lies outside of this region.

The second electrode is positioned on, or in, the body; to be precise, for example, as long as the first electrode comprises a plurality of needles, outside of a region circumscribed thereby. The second electrode is positioned in a different body region to the first electrode. The second electrode (variant A: flat electrode) can, for example, be positioned above large muscle groups or layers of fat so that individual nerves are not stimulated thereby. A second electrode as per variant B (needle-shaped electrode) can, for example, be applied in an intramuscular manner.

A short-term application of a current prior to the actual treatment can, for example, provide that (a) penetrating needle(s) is/are not situated in the vicinity of nerve roots so that there is no pain reaction or a motor reaction during the treatment. The needle(s) would otherwise need be slightly withdrawn or positioned at a different point.

As an alternative thereto, muscle twitching can also be employed in a targeted manner in certain embodiments in order to check the positioning of a needle. Muscular twitching can be triggered by electric current, for example, by virtue of electrodes being held against penetrating needles when current is applied. The stronger this twitching is, the better the needle is positioned. As was already mentioned above, it is possible, for example, by using the above-described test mode, to stimulate the individual electrodes (for example, needles) directly and to deduce the correct positioning of the electrode (for example, needle) from the reaction of the patient. A needle inserted into an inflamed painful muscle thus increases muscle twitching compared to a needle penetrating a non-inflamed muscle in the case of direct test stimulation. In the case of needles penetrating non-contractible tissue, the patient feels increased pain (burning) on the needle in the inflamed tissue compared to a non-inflamed tissue in the case of direct test stimulation.

It is optionally also possible to use a plurality of current sources that can be regulated separately.

It is possible that the electric fields generated by the direct current application device according to the present invention have a reconstructive effect in addition to their antiphlogistic and analgesic effect, for example, by promoting the vessel growth, inter alia by releasing VEGF and an influence on endothelial cells. It is furthermore possible that they lead to a movement and rearrangement of cell membrane receptors which increase the division rate of specific cells and accelerate the cell migration of epithelial cells (for example, towards the cathode) and wound healing. It is also feasible for this to be able, after spinal trauma, to accelerate the peripheral nerve regeneration by growth towards the cathode, which would then, for example, lie towards the head.

Without being bound to a specific theory, the effect of the application of the direct current application device according to the present invention on the human or animal body can be traced back to the direct effect of the administered electric current or the applied electric field on the affected tissue or the affected cells. By way of example, an explanation for this lies in a change in the electric excitability of cells, for example, nerve cells (depolarization or hyperpolarization), possibly as a result of an effect on cation channels or a temporary displacement of the ion equilibrium between intracellular and extracellular space. An efflux of potassium ions and other cations into the extracellular space will come into question therefor, for example, as a result of which a local antiphlogistic and analgesic effect could be explained. A regeneration of aseptic wounds or degeneratively changed tissue portions or migration of cells in the electric field could also be a (contributory) cause of the observed effect. Without being bound to a specific theory, the assumption is made that the administered electric current or the applied electric field directly and locally influences fundamental inflammation processes, processes in pain generation and/or in tissue regeneration in the cells and in the tissue. As a result, basic electrophysiological/neurophysiological mechanisms are influenced.

The current and voltage here are many times (several powers of 10) smaller than in known electroacupuncture appliances. Use can, for example, be made of direct current and not of alternating current.

In known medical electrostimulation appliances, the mode of operation is based on a high intensity of the voltage and/or of the current. By way of example, in the case of galvanic baths or in the case of cauterization, the tissue is to be heated, or, in the case of TENS (gate control theory), there is to be pain suppression by a supraliminal receptor stimulation. In contrast thereto, the direct current application device according to the present invention operates at very low voltages, currents and electric fields, as a result of which, for example, an anti-inflammatory, pain-inhibiting and/or regenerative effect is produced.

After penetration of a needle, a potential difference of, for example, 100-300 mV is measured between the negative pole on the needle and a large-area electrode adhesively bonded onto the skin. The potential difference can be increased by rapid manual rotation of the needle, which can primarily be traced back to influencing of the electrode contact potential, and subsequently can be reduced logarithmically to the initial value again. Penetrating of needles and the manual stimulation thereof are basic techniques in analgesic acupuncture.

The subject matter of the present invention furthermore relates to the direct current application device according to the present invention for application in the treatment of the following impairments or complaints: migraine, tension headache (for example, migraine-like tension headache), nerve pains (for example, post zoster neuralgia, occipital neuralgia, trigeminal neuralgia, neuralgia of the femoral nerve, especially post surgery), herpes zoster pain, neuropathic post zoster pain, Bing-Horton syndrome, tinnitus, allergies, inflamed signs in allergies, cervical spine syndrome, thoracic spine syndrome, lumbar spine syndrome, chronic lower back pain, neural canal stenosis, cervicobrachialgia, sciatica, radiculopathy, frozen shoulder, pain in the case of arthrosis, gonarthrosis, arthritis (to the extent that this is not systemic), tendinitis (such as tennis elbow, golfer's elbow (lateral and medial epicondylitis)), inflammation of a tendon sheath, insertion tendonitis, pain in the Achilles tendon, calcaneal spur, skin reddening, skin inflammation, seborrhea, psoriasis, seborrhoic, erythematous and/or psoriatic appearances, acne, hair loss (for example, alopecia), movement restrictions caused by local irritation, especially of the skin, such as local hardening and tension.

A corresponding statement applies to the use of the direct current application device according to the present invention for treating the aforementioned indications and to the use of the direct current application device according to the present invention for producing a therapeutic device for treatment of the aforementioned indications.

The direct current application device according to the present invention can, for example, produce a long-term regenerative effect which builds up from treatment to treatment, for example, in the case of chronic tendinitis or chronic neuropathic pain.

The following treatments can, for example, be excluded: treatment of a hair follicle, treatment of open wounds and treatment of skin damage.

In an embodiment, the present invention relates to the use of the direct current application device according to the present invention for cosmetic treatment of the human or animal body.

In an embodiment, the present invention moreover relates to a method for producing a direct current application device comprising the following steps: providing a kit according to the present invention, providing a direct current source or (if the kit contains a battery as direct current source) providing the direct current source, providing the flat electrode or the needle or electrically conductively connecting the plurality of needles to form the first electrode (wherein the tips of a plurality of needles can, for example, be arranged along a substantially circular or elliptical circumference or along a substantially straight line and the electrically conductive connection can, for example, be established along the circumference), providing the flat electrode or the needle or electrically conductively connecting the plurality of needles to form the second electrode (wherein the tips of a plurality of needles can, for example, be arranged along a substantially circular or elliptical circumference or along a substantially straight line and the electrically conductive connection can, for example, be established along the circumference), connecting the first electrode to the direct current source and connecting the second electrode to the direct current source.

In an embodiment, the present invention provides the use of the direct current application device according to the present invention in a method for the treatment of the human or animal body by therapy or the use of the direct current application device according to the present invention in a method for the treatment of the human or animal body by therapy.

The present invention finally relates to an electric field that can be produced by the direct current application device according to the present invention. The field maximum here lies around the needle body and a needle tip.

The present invention furthermore relates to such an electric field for use in a method for treatment of the human or animal body by therapy, for example, such an electric field for treatment of inflammations and/or pain, for example, of the muscles, nerves, tendons or bones, or for treatment of one of the aforementioned indications.

EXAMPLES

Example 1: Cluster Headache

Male patient, 56 years old. Bing-Horton syndrome known about for 3 years, with almost unbearable face pain attacks at irregular intervals. This is an uncommon clinical picture with extreme pain (also referred to as "suicidal headache") in which previously known therapeutic methods are not at all satisfactory. At presentation, unbearable bouts of pain daily, sometimes a number of times daily. Previous therapies were all without success (inter alia analgesics, oxygen inhalation). Treatment using the direct current application device according to the present invention: adhesive surface electrode (adhesive pad) on the upper arm as anode, four needles 0.2×15 mm as cathode are placed below the eye and 1 cm next to the left wing of the nose, needles placed in a circular shape and electrically conductively connected along the circle. Current 250 µA for 35 minutes. After the first treatment, there was an immediate reduction in the frequency of the bouts from two times daily to once in four days; pain intensity reduced by 40% (VAS). After the second treatment, complete suspension of pain attacks. The patient is without complaints to date, follow-up after 4 months.

Example 2: Cervical Spine Syndrome with Radiation into the Sixth Cervical Nerve (Radiculitis C6)

Male patient, 72 years old. Strong pain over the last 4 months in the LHS region of the cervical spine, radiating day and night, with tingling paresthesia and pain into the left neck, upper arm, forearm and to the left thumb. Previous therapy with analgesics, salves, injections without improvement. Therapy with direct current application device: adhesive pad in the left abdominal region, 8 needles (0.3×30 mm) 3 cm paravertebral LHS C5-C6, needles inserted circularly; 230 µA current for 20 minutes. First pain relief 90 minutes after therapy. Second treatment after four days. Thereafter, immediate stop of the residual complaints and the patient has been without complaints. Follow-up after 5 months.

Example 3: Foot Pain, Morton's Neuralgia

Female patient, 61 years old. Very strong pain on the fourth left toe for the past year. MRI detected wear on the interdigital nerve. Morton's neuralgia diagnosed. Conventional conservative and operative therapy methods already known for Morton's neuralgia are mainly completely unsatisfactory; the patients have very high level of suffering since they can only run with great pain in the foot. Treatment according to the present invention: adhesive pad on the left of the calf (anode), needle electrode (cathode) 8 needles (0.2×15 mm) on the fourth toe left, series connection, 60 µA current for 40 minutes. Two treatments with a time interval of seven days. Approximately 70% improvement (VAS) of the pain 1 day after the first treatment; completely without pain after the second treatment. Follow-up after 1.5 years.

Example 4: Occipital Neuralgia

Female patient, 60 years old. Fell while skiing 4 weeks ago. Since then increasing headache on the RHS of the back of the head. Injections, 3 acupuncture treatments, non-steroidal analgesics (diclofenac, ibuprofen) without effect, most recently tilidine drops for 2 weeks. High levels of suffering. The whole region of the back of the head on the RHS, with radiation into the right ear, is very sensitive to touch. Decision to undertake the therapy according to the present invention using a direct current application device: adhesive pad on the right-hand side of the upper arm, 8 needles (0.25×40 mm) in the most painful and pressure-sensitive region the back of the head and paravertebral C1-C2 on RHS, needles connected in series; 125 µA current for 30 minutes. First improvement 60 minutes after therapy. Completely without pain 3 hours later. Since then without complaints; follow-up after 2 months. Occipital neuralgias (like in this patient) can in general occur after acute traumas. The pain was unusually strong in this patient. It was possible to prevent chronification (as is otherwise common in occipital neuralgias).

Example 5: Elbow Tendonitis "Golfer's Elbow"

Male patient, 45 years old. Elbow medially at points. Previous therapy: 9 cortisone injections, four times shockwaves, physiotherapy, 10 acupuncture treatments without lasting success. Therapy according to the present invention: adhesive pad on RHS upper arm, local anesthesia on RHS elbow, 8 needles (0.3×30 mm) as electrode in the most painful and pressure-sensitive region, arranged in a circle. 270 µA. 30 minutes. First improvement 12 hours after the end of treatment, free from complaints after the second day thereafter. Lastingly free from complaints follow-up after 4 months. Surprising efficiency with only a single treatment.

Example 6: Acute Lower Back Pain with Sciatica

Female patient, 58 years old. Lumbar spine pain on RHS for 4 days, maximum point over the acupuncture points BL-25 and GB-30, radiating along the bladder meridian into the lower leg. Treatment using the direct current application device according to the present invention: adhesive pad on the LHS abdomen flank as anode, local anesthesia, elbow, as cathode: 8 needles (0.3×100 mm) in the most painful and pressure-sensitive region of the gluteal muscles, 8 further needles in the painful region of the calf, electric coupling of all needles. 250 µA. Almost without pain directly after the treatment; completely without complaints on the next day.

Example 7: Chronic Lower Back Pain in the Case of Neural Canal Stenosis

Female patient, 78 years old. Chronic lower back pain for more than 1.5 years despite conventional orthopedic therapy, more on RHS than on LHS, worsened by being seated for a relatively long time. MRI could show significant narrowing of the neural canal. 15 acupuncture treatments without substantial improvement. Therapy according to the present invention: adhesive pad on RHS flank of abdomen, local anesthesia paravertebral from L4-L5, 8 needles (0.3×100 mm) in the most painful and pressure-sensitive region paravertebral L4-L5, advance to bone contact with the small vertebral joints, 4 needles are advanced past there as far as into the vicinity of the nerve exit points. Electric coupling of all needles. 250 µA. Approximately 20% (VAS) improvement of the back pain after the first treatment, approximately 60% (VAS) improvement after the second treatment; the leg pain completely disappeared after the third treatment and there was only approximately 10% (VAS) back pain. In addition to the treatments according to the present invention, there were 4 conventional acupuncture treatments.

Example 8: Tension Headache and Migraine

Male patient, 48 years old. Headaches for 15 years, approximately 2-8 days/month. Twice per month with nausea, throbbing, pulsating pain on one side (usually RHS). Previous therapy using indometacin and other peripheral analgesics. Treatment with the direct current application device according to the present invention in the case of an acute migraine headache. Adhesive pad on RHS shoulder, 4 needles (0.3×30 mm) in the most painful and pressure-sensitive region on RHS of back of the head and 4 further needles following the progress of the pain radiation to RHS of forehead. 125 µA for 30 minutes. Improvement starting after 45 minutes; no more headache after 90 minutes. Repetition of the same therapy only in the case of acute attacks. Within 4 treatments, reduction in the headache frequency to approximately 4/year with at the same time reduction in the pain to 30% of the initial value. Follow-up after 3 years.

Example 9: Acute Shoulder Pain with Inflammation of the Subacromial Bursa and Supraspinatus Tendinitis Female patient, 48 years old. After overloading the RHS shoulder during relocation, foudroyant increase of RHS shoulder capsule pain for past 3 days. X-ray—calcium deposits in the subacromial bursa. Maximum pressure pain, slight reddening over the greater tubercle, shoulder mobility rescinded, toothache-like night pain in the RHS shoulder. Therapy according to the present invention: adhesive pad with anode on RHS flank, cathode on 4 needles (0.2×15 mm) circularly over the maximum pain on the tubercle, four needles (0.3×30 mm) into the subacromial space from the dorsal side. 125 µA, stimulation for 30 minutes. Improvement starting approximately 2 hours after the end of therapy. The shoulder is now without pain at night. Mobility in all degrees of freedom (ante-retroversion, abduction) approximately 50% more free. 2 days after therapy, recurrent pain at night. Patient is presented again for treatment. Same procedure on the greater tubercle; additionally, 4 needles (0.25×40 mm) are advanced ventrally subacromial from different sides along the extent of the supraspinatus tendon, in each case until the typical pain is triggered. Coupling all probes in a series circuit. 250 µA; 20-minute stimulation. First alleviating of pain directly after the end of the therapy. Significant improvement 4 hours later, without pain on the next day. Completely free shoulder mobility after one week. The patient is without complaints. Follow-up after 2 months.

Example 10: Inflammation of the Knee Joint Capsule in Arthrosis

Female patient, 73 years old. Gonarthrosis on both sides known for years; Kellgren stage 3-4. For the past 4 months increased pain after exertion and at night in the LHS medial knee joint capsule region. After 6 acupunctures, concentration of the pain point to the insertion of the medial collateral ligament. Therapy according to the present invention: circular penetration of 8 needles (0.3×30 mm) at the pain point and ring-shaped electric coupling. Connection to the cathode. Adhesive pad on left thigh (anode), stimulation 250 µA over 35 minutes. Approximately 50% improvement from the second day after the treatment. After one week, the same therapy. Two days later without pain. Follow-up after 5 months.

Example 11: Retropatellar Pain Syndrome with Pain at the Rectus Femoris Muscle/Patella Insertion on Both Knee Joints Male patient, 34 years old. Pain when climbing stairs and walking for a relatively long time for the past 2 years, triggered by accelerated bodybuilding training. A plurality of cortisone injections, physiotherapy, physical therapy and acupuncture treatments without success. Therapy according to the present invention: adhesive pad with anode on the flank, LHS and RHS knee under local anesthesia, in each case eight 0.3×30 mm needles, coupled in a circular shape and connected to the cathode; 260 µA over 30 minutes. 2 hours after the treatment, climbing stairs without pain is possible, wherein the pain alleviation lasts for 4 days; thereafter renewed therapy with the same procedure. Renewed presentation after 2 weeks, the patient reports an approximately 40% continuous improvement; once again same therapy; renewed presentation after 4 weeks, now overall 70% improvement; once again the same therapy; renewed presentation after 6 weeks; the patient is without complaints despite intensive bodybuilding training. Follow-up after 5 months.

Example 12: Acute Distortion of the Ankle

Male patient, 43 years old. Right foot bent when playing soccer. Swelling and pressure pain at typical position ventrolaterally of the fibular malleolus, slight livid discoloration by hematoma. The foot cannot be moved; protected limping with crutches. Therapy according to the present invention: under local anesthesia, applying 8 needles (0.25×40 mm) directly into the pain region up to the periosteum. Adhesive pad with anode onto the calf. 30-minute stimulation. Significant improvement 60 minutes after end of therapy. Further improvement the next day. Thereafter unrestricted ability to take loads again when playing soccer, despite local swelling still present. Note: in general, an ankle distortion requires 3-6 weeks to heal; the acceleration of the healing process here in the case of an acute sports injury is of interest.

Example 13: Acute Torn Muscle Fiber on Right Thigh

When playing soccer, the patient had sudden pain in the right thigh. Continuous pain under load, livid discoloration for 3 days. Ultrasound showed loosened irregular fiber structure of the vastus femoris lateralis muscle. Three acupuncture treatments without substantial improvement. Continued localized pressure pain and load pain on RHS thigh. Therapy according to the present invention: 6 needles (0.25×40 mm) circularly around the pain center; 2 needles centrally into the locus dolendi, pad with anode on RHS flank. Cathode to the needle probes, 45-minute stimulation with 110 µA. Significant pain reduction after 90 minutes. The leg was able to take loads on the next day with 80% reduction in pain. Without complaints after 4 days without further therapy; patient once again plays soccer.

Example 14: Trigeminal Neuralgia with Atypical, Permanent RHS Facial Pain

Male patient, 67 years old. Trigeminal neuralgia for the past 8 years. Started after dental treatment. State after surgery according to Janetta: pain level of 8-9 on the 11 point box scale with daily administration of pregabalin. Centering of the pain on the RHS upper lip. Therapy according to the present invention: RHS upper lip: 8 needles (0.2×25 mm), circular coupling, application of the cathode. Anode on adhesive pad on RHS upper arm. Stimulation for 30 minutes at 160 µA. 30 minutes after therapy there was a reduction of the permanent pain on the RHS upper lip to 3

(11 point box scale). Continuous improvement for 2 days. Thereafter return to original pain intensity. Patient repeated the treatment 1-2 times per week. In each case, a pain reduction for approximately 2 days.

Example 15: Tinnitus

Female patient, 73 years old; tinnitus on RHS for past 12 months. Adhesively bonding a 1 cm$^2$ adhesive electrode one finger width under the RHS mastoid, adhesively bonding a 50 cm$^2$ adhesive electrode over deltoid RHS upper arm. Connection between small electrode and anode, connection between the large electrode and the cathode. Application of 1000 µA for 45 minutes. Reduction of the tinnitus by 30% directly after the therapy, complete suspension of the tinnitus for one day after therapy, renewed tinnitus with the same volume as before the therapy on the second day after the therapy. Replication of the reaction pattern at three successive therapies with an interval of in each case 2 weeks.

Example 16: Tennis Elbow 47-year-old patient, tennis elbow on RHS for past 4 months. Adhesively bonding a 1.5 cm$^2$ adhesive electrode on the right lateral epicondyle, adhesively bonding a 50 cm$^2$ adhesive electrode over deltoid RHS upper arm. Connection between the small electrode and the anode, connection between the large electrode and the cathode. Application of 1500 µA for 60 minutes. 4-time repetition of therapy with a 2-week interval. Improvement in the elbow pain after the first therapy by 20%, by 40% after the second therapy, by 60% after the third therapy and by 80% after the fourth therapy.

Example 17: Migraine-Like Headache 51-year-old patient with throbbing headache LHS, radiating from occiput to temple, nausea, vomiting. Application of a first needle over the greater occipital nerve and a second needle on the forehead, two finger widths above the eye. Needle thickness 0.25 mm. Application of the cathode on the forehead needle and the anode on the occipital needle. Current source 3 V. Battery, current 120 µA, reducing to 20 µA over the course of the treatment. 80% improvement of the headache after 12 hours.

Example 18: Tension Headache 51-year-old patient with a dull headache on both sides, radiating from occiput to forehead. Placement of four needles occipital on pressure-pain-sensitive regions on the squama occipitalis and an adhesive pad of approximately 100 cm$^2$ on the RHS flank below the costal margin, needle thickness 0.3 mm. Application of the cathode on the flat electrode and the anode on the occipital needles. Current source 3 V. Battery, current 200 µA, reducing to 110 µA over the course of the treatment. 50% improvement of the headache after 6 hours, no headache the next day.

Example 19: Inflammation of the Supraspinatus Tendon on RHS Shoulder

Male patient, 48 years old, participant in throwing events, shoulder pain on RHS for past 5 weeks. Adhesively bonding a 2 cm$^2$ adhesive electrode over the greater tubercle of the shoulder, adhesively bonding an adhesive pad of 100 cm$^2$ on the RHS flank directly below the costal margin. Connection between small electrode and cathode, connection between large electrode and anode. Application of 1500 µA over 60 minutes. Improvement in the shoulder pain by 20% directly after the therapy, 70% improvement the next day.

Example 20: Herpes Zoster Neuralgia

Female patient, 62 years old, herpes zoster neuralgia for past 4 weeks on LHS flank, approximately T6-T9. Application of 15 0.3 mm-thick needles tangentially under the skin, directly in the painful area. Adhesive bonding of a 50 cm$^2$ adhesive electrode over the deltoid RHS upper arm. Individual connection between the needles and the cathode, connection between the adhesive electrode and the anode. Application of 500 µA for 5 minutes, then 400 µA for 5 minutes, then 50 µA for 30 minutes; improvement in the neuralgia pain by 50% on the first day after the therapy, further improvement by 50% after the same treatment was repeated after one week. 4 weeks later completely free from pain.

The present invention is not limited to embodiments described herein; reference should be had to the appended claims.

What is claimed is:

1. A direct current application device, the direct current application device comprising:
    a direct current source or an appliance configured to be linked to a direct current source;
    a first electrode configured to be connected to the direct current source, the first electrode comprising a plurality of needles comprising 3-12 needles which are configured to comprise an electrically conductive connection with each other;
    a second electrode configured to be connected to the direct current source, the second electrode comprising (i) a flat electrode, or (ii) a needle or a plurality of needles which are configured to comprise an electrically conductive connection with each other; and
    a current device configured to maintain a current at a constant level during an application of the direct current, or a battery as the direct current source,
    wherein, the direct current application device is configured to provide a maximum current of either 2,000 µA when the second electrode comprises (i) the flat electrode or 1,000 µA when the second electrode comprises (ii) the needle or the plurality of needles, and is further configured to provide an electric voltage that avoids a damaging effect on a body.

2. A kit for producing a direct current application device as recited in claim 1, the kit comprising:
    a plurality of needles comprising 3-12 needles as a first electrode;
    (i) a flat electrode, or (ii) a needle or a plurality of needles as a second electrode; and
    a current device configured to maintain a current at a constant level during an application of a direct current by a direct current source, or a battery as a direct current source
    wherein, the direct current application device is configured to provide a maximum current of either 2,000 µA when the second electrode comprises (i) the flat electrode or 1,000 µA when the second electrode comprises (ii) the needle or the plurality of needles, and is further configured to provide an electric voltage that avoids a damaging effect on a body.

3. The kit as recited in claim 2, further comprising an electrically conductive connection for the plurality of needles.

4. A method for producing a direct current application device, the method comprising:
    providing the kit as recited in claim 2;
    providing a direct current source;

connecting the plurality of needles so as to be electrically conductive to form the first electrode;

providing the flat electrode or the needle, or connecting the plurality of needles so as to be electrically conductive, to form the second electrode;

connecting the first electrode to the direct current source; and connecting the second electrode to the direct current source.

5. The direct current application device as recited in claim 1, wherein each of the plurality of needles comprise tips which are arranged along a substantially circular circumference or along a substantially elliptical circumference.

6. The direct current application device as recited in claim 5, wherein the electrically conductive connection is formed along the substantially circular circumference or along the substantially elliptical circumference.

7. The direct current application device as recited in claim 1, wherein the current device is further configured to be automated.

8. The direct current application device as recited in claim 1, wherein the first electrode is provided as a cathode.

9. A method for the treatment of at least one of an inflammation and a pain in a patient, or for a cosmetic treatment of a human body or an animal body, the method comprising:

providing a direct current application device comprising:
a direct current source or an appliance configured to be linked to a direct current source,
a first electrode configured to be connected to the direct current source, the first electrode comprising a plurality of needles comprising 3-12 needles which are configured to comprise an electrically conductive connection with each other,
a second electrode configured to be connected to the direct current source, the second electrode comprising (i) a flat electrode, or (ii) a needle or a plurality of needles which are configured to comprise an electrically conductive connection with each other, and
a current device configured to maintain a current at a constant level during an application of the direct current, or a battery as the direct current source; and
allowing the direct current application device to act on the human body or on the animal body,
wherein, the direct current application device is configured to provide a maximum current of either 2,000 µA when the second electrode comprises (i) the flat electrode or 1,000 µA when the second electrode comprises (ii) the needle or the plurality of needles, and is further configured to provide an electric voltage that avoids a damaging effect on the human body or on the animal body.

10. The method as recited in claim 9, wherein the inflammation and/or the pain is in at least one of a muscle, a nerve, a tendon and a bone.

11. A method for treating an inflammation and/or a pain in a patient with a direct current application device, the method comprising:

providing a direct current application device comprising:
a direct current source or an appliance configured to be linked to a direct current source,
a first electrode configured to be connected to the direct current source, the first electrode comprising a flat electrode, a needle, or a plurality of needles which are configured to comprise an electrically conductive connection with each other,
a second electrode configured to be connected to the direct current source, the second electrode comprising (i) a flat electrode, or (ii) a needle or a plurality of needles which are configured to comprise an electrically conductive connection with each other, and
a current device configured to maintain a current at a constant level during an application of the direct current, or a battery as the direct current source; and
allowing the direct current application device to act on the patient,
wherein, the direct current application device is configured to provide a maximum current of either 2,000 µA when the second electrode comprises (i) the flat electrode or 1,000 µA when the second electrode comprises (ii) the needle or the plurality of needles, and is further configured to provide an electric voltage that avoids a damaging effect on a body.

12. The method as recited in claim 11, wherein the inflammation and/or the pain is in at least one of a muscle, a nerve, a tendon and a bone of the patient.

13. A method of treating an inflammation and/or a pain in a patient, the method comprising, providing a direct current application device comprising:
a direct current source or an appliance configured to be linked to a direct current source,
a first electrode configured to be connected to the direct current source, the first electrode comprising a flat electrode, a needle, or a plurality of needles which are configured to comprise an electrically conductive connection with each other,
a second electrode configured to be connected to the direct current source, the second electrode comprising (i) a flat electrode, or (ii) a needle or a plurality of needles which are configured to comprise an electrically conductive connection with each other, and
a current device configured to maintain a current at a constant level during an application of the direct current, or a battery as the direct current source,
wherein, the direct current application device is configured to provide a maximum current of either 2,000 µA when the second electrode comprises (i) the flat electrode or 1,000 µA when the second electrode comprises (ii) the needle or the plurality of needles, and is further configured to provide an electric voltage that avoids a damaging effect on a body;
generating an electric field with the direct current application device;
causing the direct current application device to generate an electric field; and
allowing the electric field to act on the patient.

14. The method as recited in claim 13, wherein the inflammation and/or the pain is in at least one of a muscle, a nerve, a tendon and a bone.

* * * * *